(12) United States Patent
Subramanian et al.

(10) Patent No.: US 7,326,672 B2
(45) Date of Patent: Feb. 5, 2008

(54) SUBSTANTIALLY ENZYME FREE PERSONAL WASH COMPOSITIONS COMPRISING NON-SILICATES WITH BASAL LAYER CATIONIC CHARGE

(76) Inventors: Vivek Subramanian, 25 W. Cedar St., Livingston, NJ (US) 07039; Pravin Shah, 83 Woodward Ave., Rutherford, NJ (US) 07070; Kavssery Parameswaran Ananthapadmanabhan, 23 Vanderbilt Dr., Highland Mills, NJ (US) 10930

( * ) Notice: Subject to any disclaimer, the term of this patent is extended or adjusted under 35 U.S.C. 154(b) by 271 days.

(21) Appl. No.: 10/902,202

(22) Filed: Jul. 29, 2004

(65) Prior Publication Data

US 2006/0025319 A1 Feb. 2, 2006

(51) Int. Cl.
*C11D 1/02* (2006.01)
*C11D 3/44* (2006.01)
*C11D 7/10* (2006.01)

(52) U.S. Cl. .................. 510/137; 510/130; 510/155; 510/367; 510/374; 510/417; 510/422; 510/432; 510/508

(58) Field of Classification Search .......... 510/130, 510/137, 155, 367, 374, 417, 422, 432, 508
See application file for complete search history.

(56) References Cited

U.S. PATENT DOCUMENTS

| | | | | |
|---|---|---|---|---|
| 5,145,599 A | * | 9/1992 | Endres et al. ............. 8/137 |
| 5,149,456 A | * | 9/1992 | Concannon et al. ....... 510/348 |
| 5,501,814 A | * | 3/1996 | Engelskirchen et al. .... 510/471 |
| 5,661,189 A | * | 8/1997 | Grieveson et al. ......... 514/784 |
| 5,783,543 A | * | 7/1998 | Fleckenstein et al. ...... 510/280 |
| 5,786,381 A | * | 7/1998 | Franklin et al. .......... 514/557 |
| 5,814,323 A | * | 9/1998 | Lyle ...................... 424/401 |
| 6,255,264 B1 | * | 7/2001 | Fleurot et al. ............ 510/124 |
| 2003/0211062 A1 | * | 11/2003 | Laden et al. ............. 424/70.1 |
| 2004/0102446 A1 | * | 5/2004 | Pflucker et al. ........... 514/250 |
| 2005/0123487 A1 | * | 6/2005 | Spadini et al. ............ 424/47 |

FOREIGN PATENT DOCUMENTS

JP 03190811 * 8/1991

OTHER PUBLICATIONS

Patent Abstracts of Japan, vol. 015, No. 445 (C-0884), Nov. 13, 1991 & PJ 03 190811 A (Shiseido Co., Ltd.), Aug. 20, 1991.
Written Opinion of the International Searching Authority, International Application No. PCT/EP2005/007539.
Luckham et al., *The colloidal and rheological properties of bentonite suspensions*, Advances in Colloid and Interface Science, 82 (1999) pp. 43-92.
Written Opinion of the International Searching Authority, International Application No. PCT/EP2005/007539, no date available.

* cited by examiner

*Primary Examiner*—Charles Boyer
(74) *Attorney, Agent, or Firm*—Ronald A. Koatz

(57) ABSTRACT

The present invention relates to personal wash compositions comprising, non-silicate particles, wherein the basal layer(s) carries a net cationic charge. The use of these specific particles results in enhanced properties (e.g., enhanced foaming, hydrotroping) of the personal wash products. The invention further discloses process for decreasing viscosity and/or increasing foam comprising formulating compositions with non-silicate layer compounds as specified.

2 Claims, 2 Drawing Sheets

"Cationic Clay" Anionic charge in basal layer

"Anionic Clay" Anionic charge in interstitial layer

SUBSTANTIALLY ENZYME FREE PERSONAL WASH COMPOSITIONS COMPRISING NON-SILICATES WITH BASAL LAYER CATIONIC CHARGE

FIELD OF THE INVENTION

The subject invention relates to personal wash compositions, particularly those comprising non-silicate particles having cationic charge on their basal layer. Use of such specific non-silicates results in improved properties as noted below.

BACKGROUND OF THE INVENTION

It is known to use layered aluminosilicates or magnesium silicates in liquid cleansing and detergent compositions to modify the rheology of the composition. The art discloses, however, that these silicate clays are used to thicken (increase the viscosity) of the liquid composition. Typically, increased viscosity is accomplished by swelling or expanding of the silicates when they are in contact with water to form a "house of cards" structure. It is also commonly accepted (see for example, Luckham et al., *Adv. Colloid Interface Sci,* 82 (1999), 43-92.) that this house of cards structure arises from various interactions between the edges and faces of the layered clays.

Typically, the silicates (e.g., aluminosilicas) have a net negative charge on the basal plane in aqueous solutions, which arises from an isomorphous substitution of certain atoms in their structure for other atoms of a different valence. Thus, for example, $Si^{4+}$ may be replaced by $Al^{3+}$ in the lattice leading to a net negative charge on the basal plane. Such clays are called "cationic" clays because the net negative charge on the basal plane is compensated by the presence of cations in the interstitial layer. It is the hydration and dissolution of these interstitial cations that leads to swelling of the clays and the subsequent thickening effect for which they are commonly known. FIG. 1 is a schematic drawing showing typical structure with net anionic charge in the basal layer and cationic charge in the interstitial layer.

By contrast, in the subject invention it is critical that the clay be a non-silicate clay. A typical example of such clays are layered double hydroxides. Typically, these compounds have formula corresponding to the general formula:

$$Mg_xAl(OH)_y \cdot A_z \cdot nH_2O$$

in which A represents an equivalent of a non-silicate anionic and the conditions $1<X<5$, $(y+z)=2x+3$, $0<n<10$ apply.

In such clays, the metal cation in the lattice is often substituted for one of a higher valence, which leads to a positive charge on the basal plane. This is thus the opposite of the silicates described above. Such clays are often referred to as "anionic clays" because the positive charge on the basal plane is balanced by the presence of anions like $CO_3^{2-}$ or $NO_3^{-}$ in the interstitial layer.

In the present invention, applicants have found that the addition of the anionic (non-silicate) clay to personal wash compositions, unexpectedly, lowers the viscosity of the composition, thus acting as a hydrotrope (e.g., viscosity thinner rather than viscosity thickener). While not wishing to be bound by theory, the anionic clay is believed to help break down the mesostructure of surfactants used in the subject invention, thereby leading to easy dispersibility and ready incorporation of air (hence better foam).

U.S. Pat. No. 5,145,599 to Endres et al. does disclose the type of non-silicate layer compounds (having positive charge on basal layer) used in the subject invention. However, in the patent, the compounds are used in enzyme-containing, fabric-cleansing detergent compositions. Such detergent compositions are not concerned with lather, mildness or other attributes which the personal cleansing compositions of the subject invention relate to.

U.S. Pat. No. 5,661,189 to Grieveson et al. discloses that hydrotalcites can be used as a thickening agent (column 2, line 67). They are one of many potential "thickening agents" and there is clearly no teaching or suggestion that, if used at all, they serve to reduce viscosity. The present invention is a selection patent in which hydrotalcite must be used.

BRIEF DESCRIPTION OF THE INVENTION

Unexpectedly, applicants have found that when non-silicate clays having basal layer with cationic charge are used in personal wash compositions (i.e., substantially enzyme-free personal wash compositions), the clays interact with surfactants in the personal wash compositions to breakdown the surfactant mesostructure. This in turn results in easy dispersibility (i.e., lower viscosity), better foam (easier incorporation of air) and reduced irritation. It also can improve delivery of actives.

More particularly, in one embodiment, the present invention provides compositions comprising:

(1) about 5 to 35%, preferably 5% to 30% by wt. of a surfactant selected from the group consisting of anionic, nonionic, zwitterionic/amphoteric and cationic surfactants and mixtures thereof;

(2) about 0.1 to 15%, preferably 0.5 to 10%, more preferably 0.2 to 5% by wt of a non-silicate layer compound, wherein a net cationic charge is found in the basal layer;

(3) about 3 to 40%, preferably 5 to 30% by wt. of an aqueous solvent; and (4) about 5 to 40% by wt. non-aqueous solvent;

wherein said composition is substantially enzyme free.

In a second embodiment, the invention provides a process to decrease viscosity and/or enhance foam in substantially enzyme-free personal wash composition which process comprises formulating non-silicate layer compounds as noted above into the personal wash compositions.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different end points are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

Figure 1:
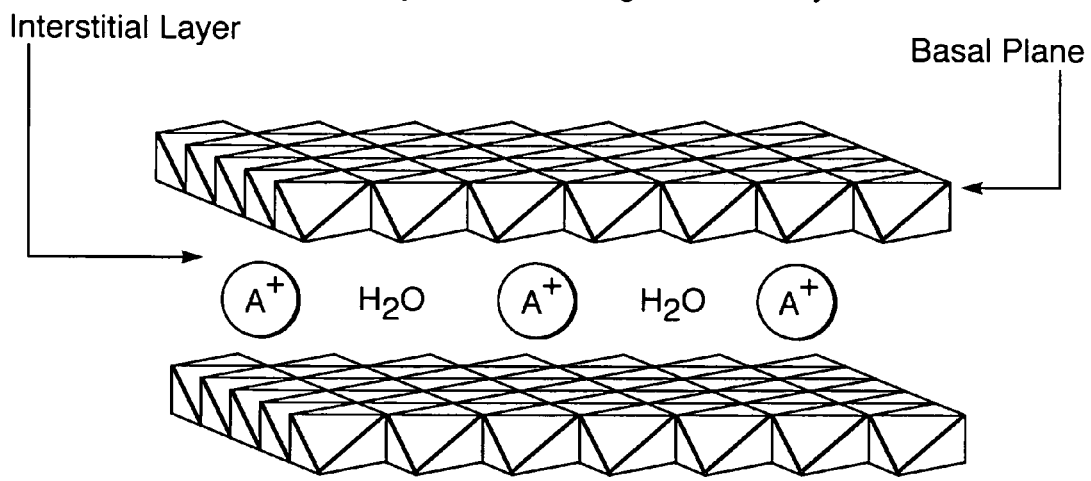
FIG. 1 is a schematic drawing of a typical silicate layered compound ("cationic" clay) having net anionic charge on basal layer.

In one embodiment, the present invention relates to personal wash compositions (substantially enzyme free) comprising non-silicate, layer compounds having a net cationic charge on the basal layer. Unexpectedly, applicants have found that surfactants present in such compositions interact with and are broken down by the non-silicate compound (e.g., mesostructure broken down) resulting in multiple sensory and/or other benefits to the consumer (more foam, less irritation, etc.).

Specifically, the invention comprises:
(1) about 5 to 35%, preferably 5% to 30% by wt. of a surfactant selected from the group consisting of anionic, nonionic, zwitterionic/amphoteric and cationic surfactants and mixtures thereof;
(2) about 0.1 to 15%, preferably 0.5 to 10%, more preferably 0.2 to 5% by wt of a non-silicate layer compound wherein a net cationic charge is found on the basal layer;
(3) about 3 to 40%, preferably 5 to 30% by wt. of an aqueous solvent; and
(4) 5 to 40% by wt. non-aqueous solvent
wherein the composition is substantially enzyme free.

In preferred embodiments, at least 50% of surfactant system should be anionic surfactant. Preferably, the combination comprises 5-25% by wt. of an anionic or mixture of anionic surfactant and 1-10% by wt. zwitterionic and/or amphoteric surfactant.

The invention is described with more particularity below:

Surfactant

As noted, the surfactant of the invention may be an anionic, nonionic, zwitterionic/amphoteric or cationic surfactant or mixtures thereof. Typically, the cleanser will be an aqueous cleanser comprising 5-25% of an anionic surfactant and 1-10%, preferably 3 to 10% of a second anionic and/or amphoteric surfactant.

The anionic surfactant may be a synthetic surfactant or fatty acid soap.

The term "soap" is used here in its popular sense, i.e., the alkali metal or alkanol ammonium salts of aliphatic alkane- or alkene monocarboxylic acids. Sodium, potassium, mono-, di and tri-ethanol ammonium cations, or combinations thereof, are suitable for purposes of this invention. In general, sodium soaps are used in the compositions of this invention, but from about 1% to about 25% of the soap may be potassium soaps. The soaps useful herein are the well known alkali metal salts of natural or synthetic aliphatic (alkanoic or alkanoic) acids having about 12 to 22 carbon atoms, preferably about 12 to about 18 carbon atoms. They may be described as alkali metal carboxylates of acrylic hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. The proportion will be greater when mixtures of coconut oil and fats such as tallow, palm oil or non-tropical nut oils or fats are used, wherein the principle chain lengths are $C_{16}$ and higher. Preferred soap for use in the compositions of this invention has at least about 85% fatty acids having about 12-18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are general exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 15% to about 20% coconut oil and about 80% to about 85% tallow. These mixtures contain about 95% fatty acids having about 12 to about 18 carbon atoms. The soap may be prepared from coconut oil in which case the fatty acid content is about 85% of $C_{12}$-$C_{18}$ chain length.

The soaps may contain unsaturation in accordance with commercially acceptable standards. Excessive unsaturation is normally avoided.

The anionic may also be an alkyl sulfate (e.g., $C_{12}$-$C_{18}$ alkylsulfate) or alkyl ether sulfate (including alkyl glycerol ether sulfates). Among the alkyl ether sulfates are those having the formula:

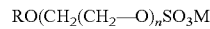
RO(CH$_2$(CH$_2$—O)$_n$SO$_3$M herein R is an alkyl or alkenyl having 8 to 18 carbons, preferably 12 to 18 carbons; n has an average value of greater than 1.0, preferably greater than 3: and M is a solubilizing cation such as sodium, potassium ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, alkyl glycosides and acyl isethionates.

Sulfosuccinates may be monoalkyl sulfosuccinates having the formula:

R$^4$O$_2$CCH$_2$CH(SO$_3$M)CO$_2$M;

and
amide-MEA sulfosuccinates of the formula

R$^4$CONHCH$_2$CH$_2$O$_2$CCH$_2$CH(SO$_3$M)CO$_2$M wherein R$^4$ ranges from $C_8$-$C_{22}$ alkyl and M is a solubilizing cation.

Sarcosinates are generally indicated by the formula

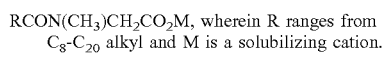
RCON(CH$_3$)CH$_2$CO$_2$M, wherein R ranges from
C$_8$-C$_{20}$ alkyl and M is a solubilizing cation.

Taurates are generally identified by formula:

R$^2$CONR$^3$CH$_2$CH$_2$SO$_3$M wherein R$^2$ ranges from C$_8$-C$_{20}$ alkyl, R$^3$ ranges from C$_1$-C$_4$ alkyl and M is a solubilizing cation.

Other anionic groups which may be used include glutamates (e.g., acyl glutamates such as sodium acyl glutamate); lysinates; alaninates; and glycinates.

Particularly preferred are the C$_8$-C$_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 5% to about 20% by weight of the total composition. Preferably, this component is present from about 5% to about 10%.

In general the anionic component will comprise from about 1 to 40% of the composition, preferably 3 to 25% by wt. of the composition.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

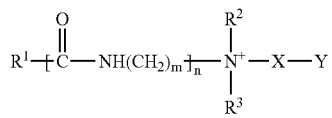

wherein R$^1$ is alkyl or alkenyl of 7 to 18 carbon atoms:
R$^2$ and R$^3$ are each independently alkyl, hydroxyalkyl or carboxyalkyl of 1 to 3 carbon atoms;
m is 2 to 4;
n is 0 to 1
X is alkylene of to 3 carbon atoms optionally substituted with hydroxyl, and
Y is —CO$_2$— or —SO$_3$—

Suitable amphoteric detergents within the above general formula include simple betaines of formula:

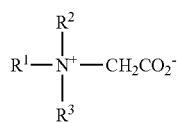

and amido betaines of formula:

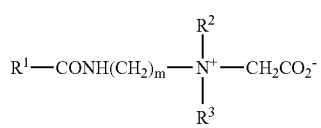

where m is 2 or 3;

In both formulae R$^1$, R$^2$ and R$^3$ are as defined previously. R$^1$ may in particular be a mixture of C$_{12}$ and C$_{14}$ alkyl groups derived from coconut so that at least half, preferably at least three quarters of the groups R$^1$ have 10 to 14 carbon atoms. R$^2$ and R$^3$ are preferably methyl.

A further possibility is that the amphoteric detergent is a sulphobetaine of formula:

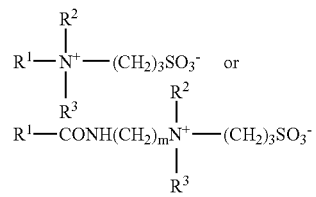

where m is 2 or 3, or variants of these in which —(CH$_2$)$_3$SO$_3$— is replaced by:

In these formula R$^1$, R$^2$ and R$^3$ are as discussed previously.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl (C$_6$-C$_{22}$) phenols-ethylene oxide condensates, the condensation products of aliphatic (C$_8$-C$_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Ser. No. 816,419 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr., which is also incorporated into the subject application by reference.

Non-Silicate Layer Compounds

The present invention relates to the use of non-silicate layer compounds corresponding to general formula (I)

Mg$_x$Al(OH)$_y$A$_z$·nH$_2$O in which A represents an equivalent of a non-silicate anionic and the conditions 1<X<5, (y+z)=2x+3, 0<n<10 apply in phosphate-reduced detergent compositions, the cationic layer compounds belonging to the structure type of hydrotalcite with a lattice distance for the most intensive line in the X-ray diffractogram of from 7.4 to 8 Å (angstroms) for the product dried at 110° C.

The basal layer of these compounds carries a net cationic charge.

Figure 2:
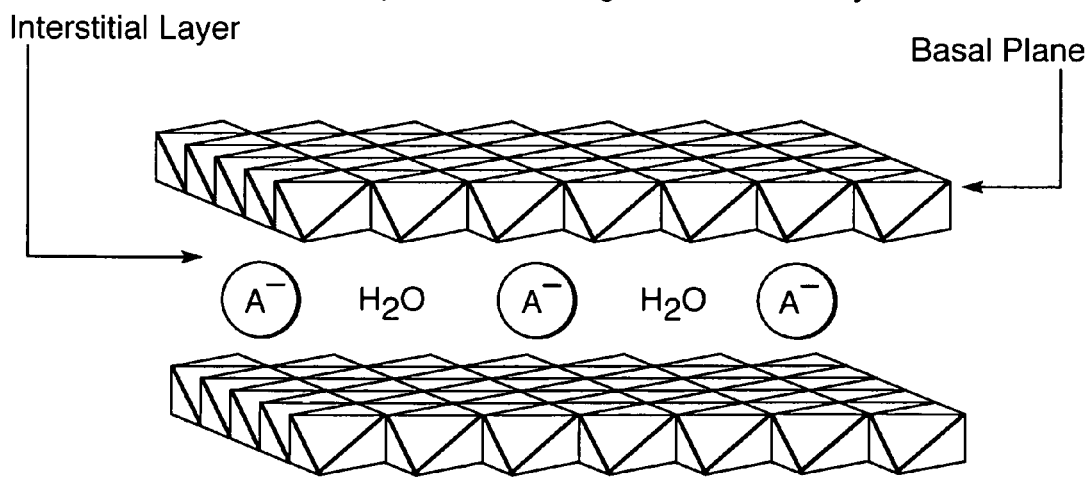
FIG. 2 is schematic of a typical non-silicate layered compound of the invention ("anionic" clay) having net cationic charge on basal layer.

In the context of the invention, these layer compounds are understood to be solids of which the structure is derived from the layer-form magnesium hydroxide, brucite, by the partial replacement of the divalent metal ions by trivalent metal ions. The resulting positive excess charge of the metal hydroxide layers is compensated by exchangeable anions between the layers. Hydrotalcite may be used as a model substance for this class of solids. A schematic of such compound is shown in FIG. 2.

Hydrotalcite is a substance occurring in nature as a mineral having the approximate composition

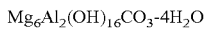

the ratio of Mg to Al and, hence, the carbonate content being variable within relatively wide limits. The carbonate may be replaced by other anions. By contrast, the substance is characterized by its layer structure with the layer sequence ABAB . . . , where A is a positively charged triple layer of hydroxyl ions, metal cations and more hydroxyl ions. B is an intermediate layer of anions and water of crystallization. This layer structure is shown up in an X-ray powder diagram which may be used for characterization. Thus, ASTM Card No. 14-191 gives the lines for the lattice plane spacings d=7.69, 3.88, 2.58, 2.30, 1.96, 1.53 and 1.50 Å as the most intensive X-ray interferences. The spacing 7.69 Å is the basic repetition period of the layers (=layer spacing) of the substance which normally contains water of crystallization. More rigorous drying at elevated temperature (120° to 200° C. a normal pressure) leads to reduced layer spacings through release of the water of crystallization.

The crystal structure of natural hydrotalcite was determined radiographically by Allmann and Jepsen (N. Jahrb. Mineral. Monatsch. 1969, pages 544-551). The range of variation of the Mg to Al ratio and its influence on the repetition period of the layers was investigated, for example, by Gastuche, Brown and Mortland (Clay Miner. & (1967), pages 177-192). Possible processes for the commercial production of synthetic hydrotalcite and its use as an agent for binding stomach acid were described in 1967 by Kyowa Chemical Indlustryu Co., Tokyo (DE-OS 15 92 126). Apart from neutralizing stomach acid, hydrotalcite may generally be used for binding acidic components, for example impurities from catalytic processes (DE-OS 27 19 024) or unwanted dyes (DE-OS 29 29 991). Further potential applications are in the field of corrosion prevention (DE-OS 31 28 716), the stabilization of plastics, particularly PVC (DE-PS 30 19 632), in waste water treatment (JP-PS 79 24 993, JP-PS 58 214 388) and in the production of colored pigments (JP-PS 81 98 265).

The incorporation of carbonate ions as intermediate layer anions is particularly preferred. Hydrotalcite-like solids containing other anions may be obtained by using a soluble salt of another acid instead of sodium carbonate in the production process or by removing the carbonate from the carbonate-containing product in the form of $CO_2$ by reaction with weak acids. The exchange of the anions is shown up in the X-ray diffractogram by a change in the layer spacings (T. Reichle, Chemtech. January 1986, pages 58-63).

Another embodiment of the present invention is characterized by the use of non-silicate layer compounds in which A in general formula (I) represents an equivalent of a carbonate ion.

Another preferred embodiment of the present invention is characterized by the use of cationic non-silicate layer compounds corresponding to general formula (I) in a quantity of from 0.1 to 15% by weight, based on the detergent composition. The use of 0.5 to 10% by weight of the cationic non-silicate layer compounds, based by the composition, is particularly preferred.

Aqueous Solvent

The compositions of the invention are generally aqueous solvent compositions wherein the aqueous solvent (e.g., water) comprises 3 to 40% by wt. of composition.

Non Aqueous

The non aqueous solvent comprises about 5 to 40% by wt. of composition. This solvent may be oils (e.g., sunflower oil), low MW fatty acids, glycols, polyols, etc. In fact, for purposes of the invention, the non-aqueous solvent may be defined as non-water solvent since it can be any solvent other than water itself.

The ratio of non aqueous to aqueous may range from 0.7:1 to 2:1.

Optional

The liquids of this invention may be isotropic single phase liquids or they may be structured as defined and using structurants as defined in U.S. Pat. No. 5,952,286 to Puvvada et al. hereby incorporated by reference into the subject invention.

The compositions may contain oils or emollients as noted below.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: Acytylatelte lanolin alcohols, lanolin, lard, mink oil and tallow.

Fatty acids and alcohols: Behenic acid, palmitic acid, stearic acid, behenyl alcohol, cetyl alcohol, eicosanyl alcohol and isocetyl alcohol.

Other examples of oil/emollients include mineral oil, petrolatum, silicone oil such as dimethyl polysiloxane, lauryl and myristyl lactate.

It should be understood that where the emollient may also function as a structurant, it should not be doubly included such that, for example, if the structurant is 15% oleyl alcohol, no more than 5% oleyl alcohol as "emollient" would be added since the emollient (whether functioning as emollient or structurant) never comprises more than 20%, preferably no more than 15% of the composition.

The emollient/oil is generally used in an amount from about 1 to 20%, preferably 1 to 15% by wt. of the composition. Generally, it should comprise no more than 20% of the composition.

In addition, the compositions of the invention may include optional ingredients as follows:

Organic solvents, such as ethanol; auxiliary thickeners, such as carboxymethylcellulose, magnesium aluminum silicate, hydroxyethylcellulose, methylcellulose, carbopols, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300);

preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used include Quatrisoft LM-200 Polyquaternium-24, Merquat Plus 3330—Polyquaternium 39; and Jaguar® type conditioners.

Polyethylene glycols which may be used include: PEG-200 to PEG-8000

| Polyox | WSR-205 | PEG 14M, |
| Polyox | WSR-N-60K | PEG 45M, or |
| Polyox | WSR-N-750 | PEG 7M. |

Thickeners which may be used include Amerchol Polymer HM 1500 (Nonoxynyl Hydroethyl Cellulose); Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt).

Another optional ingredient which may be added are the deflocculating polymers such as are taught in U.S. Pat. No. 5,147,576 to Montague, hereby incorporated by reference.

Another ingredient which may be included are exfoliants such as polyoxyethylene beads, walnut sheets and apricot seeds.

EXAMPLES

Protocols:
Viscosity measurements for examples which follow were conducted using two different methods:
(1) For model surfactant/particles system (as shown in Table 1): The viscosity of the above model surfactant/particles samples were measured using Haake RV20 Rotovisco Rheometer in a SV1 cup and bob @ 25° C.
(2) For the facial cleanser formulations (shown in Table 2) Viscosity of the above model Prototype samples as shown in table # 3, were measured using ARES Rheometer @ 25° C. using cone and plate geometry.

Foam Volume measurements were conducted as follows:
0.5 g of sample was diluted with 5 g. of DI water. Foam was generated by rubbing both the hands 10 times in a circular motion. All the foam was collected and the weight of the foam was obtained. Also the specific gravity of the foam is obtained by measuring the weight of the foam in small petri dish of known volume. Total foam volume is calculated by dividing total foam weight by foam specific gravity.

Definitions:
SLES=Sodium lauryl ether sulfate
CAPB=Cocoamidopropyl betaine

Example 1 and Comparatives A and B

The following example shows the hydrotroping (thinning) effect of hydrotalcite compared to conventional clay on surfactant mixtures (e.g., SLES-Betaine mixtures). The formulations were made by adding SLES, Betaine and water; and mixing the components using an overhead stirrer. The clays were then added and dispersed using a ultrasonic probe (model Sonic Vibracell VC 130 PB using ½" probe). Viscosity measurements (Graphed in FIG. 3) were performed immediately as set forth in the Protocol Section.

TABLE # 1

| Formulation | SLES/Betaine (60:40 ratio) | Clay (level wt. %) | Water |
|---|---|---|---|
| Comparative A (no clays) | 20 | 0 | 80 |
| Comparative B (basal layer anionic) | 20 | Bentonite (5%) | 75 |
| Example 1 (Basal layer cationic) | 20 | Hydrotalcite (5%) | 75 |

Figure 3:
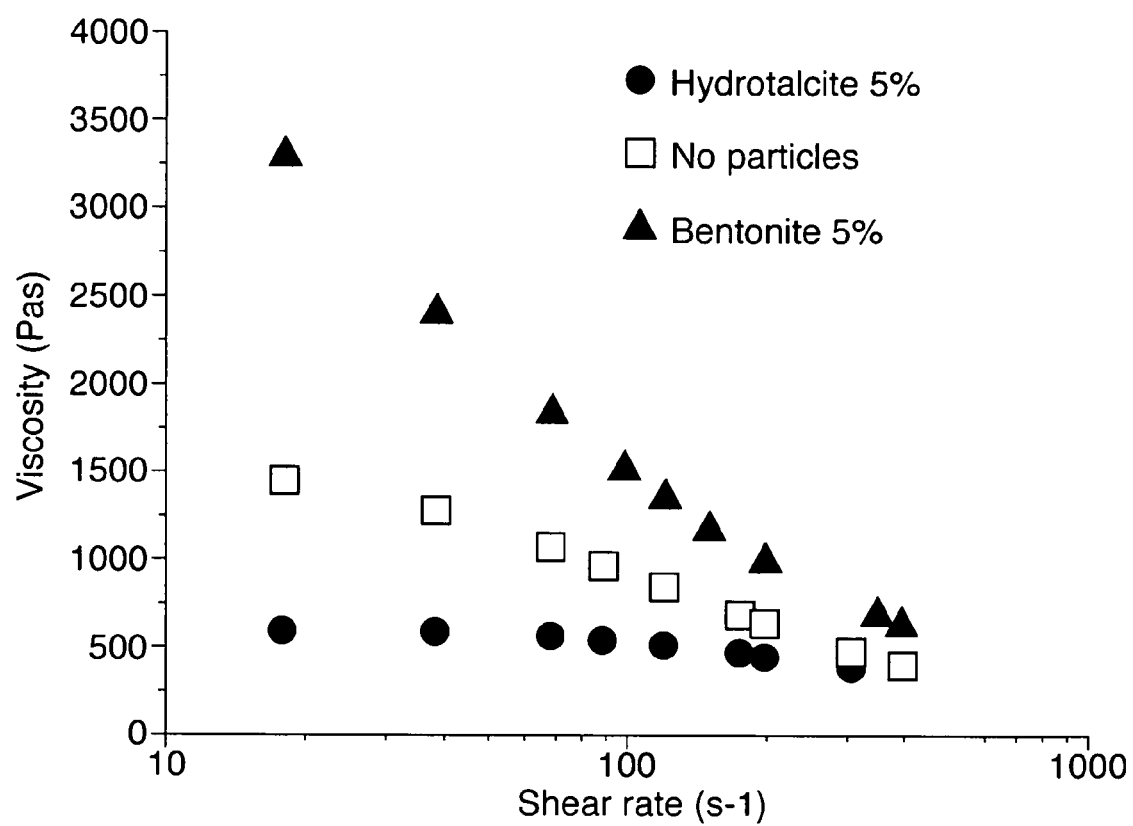
FIG. 3 shows how addition of non-silicate clays of the invention actually has hydrotroping (thinning effect) rather than a thickening effect normally expected from use of clays.

As seen in FIG. 3, relative to use of no clay, the traditional "clay" (bentonite) has a thickening effect while, unexpectedly clays of the invention have thinning effect.

Specifically, the above example clearly shows that the addition of hydrotalcite reduces the viscosity of SLES-Betaine solutions by a factor of ~3, whereas bentonite at the same level increases viscosity by a factor of ~2 at shear rates <100 s$^{-1}$.

Example 2 and Comparative C-H

The following examples show the effect of hydrotalcite and bentonite on the viscosity and lather for two facial cleanser compositions. The samples were prepared as follows:
1. Water+glycerine+PEG were added in the jacketed flask and mixed using overhead stirrer while heating;
2. Particles (e.g., clays, if any) were added while mixing until they dispersed uniformly. (Sonicating the mixture if needed);
3. Na-Glycinate was added when the temperature reached ~40° C. and was mixed until dissolved;
4. Taurate and CAPB were added while mixing until the sample was uniform;
5. Citric acid was dissolved in water and added slowly and the sample was mixed well until it looked uniform;
6. The pH was checked while mixing and adjusted to 7.0±0.5;
7. Preservative was added when temperature was ~40° C.

TABLE 2

| Material trade name | Chemical Name | Prototype Formulations | | | | | | |
|---|---|---|---|---|---|---|---|---|
| | | Comp. C | Comp. D | Example 2 | Comp. E | Comp. F | Comp. G | Comp. H |
| Glycinate | Sodium N-cocoyl Glycinate | 15.00 | 15.00 | 15.00 | 15.00 | 15.00 | 15.00 | 15.00 |
| Taurate | Sodium N-cocoyl N-methyl Taurate | 2.70 | 2.70 | 2.70 | 2.70 | 2.70 | 2.70 | 2.70 |
| CAPB | Cocamidopropyl Betaine | 1.90 | 1.90 | 1.90 | 1.90 | 1.90 | 1.90 | 1.90 |

TABLE 2-continued

Prototype Formulations

| Material trade name | Chemical Name | Comp. C | Comp. D | Example 2 | Comp. E | Comp. F | Comp. G | Comp. H |
|---|---|---|---|---|---|---|---|---|
| Glycerine | Glycerine | 20.00 | 20.00 | 20.00 | 20.00 | 20.00 | 20.00 | 40.00 |
| PEG-400 | Polyethylene Glycol | 20.00 | 20.00 | 20.00 | 20.00 | 20.00 | 20.00 | 0.00 |
| Citric acid | Citric acid | 0.70 | 0.70 | 0.70 | 0.70 | 0.70 | 0.70 | 0.70 |
| Jaguar-14-s | Cationic polymer | 0.20 | 0.20 | 0.10 | 0.20 | 0.20 | 0.20 | 0.20 |
| Mekkins | Methyl Parahydroxybenzoate | 0.01 | 0.01 | 0.01 | 0.01 | 0.01 | 0.01 | 0.01 |
| Bentonite | Clay | 2.00 | | | | | | |
| Kaoline | Clay | | 2.00 | | | | | |
| Hydrotilcite-C300 | Clay | | | 2.00 | | | | |
| Titanium Dioxide | | | | | 1.00 | 2.00 | | |
| Talc | Talc 1885 | | | | | | 2.00 | |
| H$_2$O | | 37.49 | 37.49 | 36.59 | 37.49 | 37.49 | 39.49 | 39.49 |

Table 3 below sets forth the specific clay used in the formulations as well as measured results for foam and viscosity (measured as described in Protocol of the invention). Viscosity results were tested specifically for one clay wherein basal layers has net anionic charge (bentonite), for one clay where basal layer has net cationic charge (hydrotalcite); and for formulation with no clay (Comparative G). Foam results were taken for all.

TABLE 3

| Formulation | Particle-Name | Foam Volume (ml) | Viscosity @ 0.1 (s$^{-1}$) |
|---|---|---|---|
| Comparative C | Bentonite | 20.17 | 437 |
| Comparative D | Kaoline | 14.63 | |
| Example 2 (Invention) | Hydrotilcite-C300 | 45.0 | 95 |
| Comparative E | Titanium Dioxide | 16.0 | |
| Comparative F | Talc | 19.20 | |
| Comparative G (control with no particles) | No-Particles 20% glycerin is replaced by PEG (FCAT) | 13.60 | 299 |
| Comparative H (Control with no particles) | No particles | 15.52 | |

As clearly shown from Table 3, the addition of hydrotalcite reduces the viscosity of the formulation by a factor of about 3 whereas bentonite, at the same level, increases viscosity by a factor of about 1.5, when measuring at shear rates of 0.1 S$^{-1}$ as defined in the Protocol. Also, talc and bentonite increase foam volume slightly, while hydrotalcite increases the foam volume by a factor of about 3. This is believed to be related to the reduced viscosity and easy dispersibility of the product.

The invention claimed is:

1. A personal wash composition comprising:
   (1) about 5 to 25% by wt. of a surfactant system selected from the group consisting of:
      (a) an anionic surfactant;
      (b) a mixture of anionic surfactants; or
      (c) a mixture of one or more anionic surfactants and an additional zwitterionic/amphoteric surfactant wherein the additional zwitterionic/amphoteric surfactant is present in an amount from 1 to 10% by weight;
   (2) about 0.1 to 15% by wt of a non-silicate layer compound wherein a net cationic charge is found on the basal layer or layers;
   (3) about 36.59 to 40% by wt. of an aqueous solvent which is water; and
   (4) 5 to 40% by wt. non-aqueous solvent selected from the group consisting of low MW fatty acids, glycols, polyols, and mixtures thereof;
   wherein said composition is a liquid composition and is substantially enzyme free, said composition enhances foam relative to compositions without non-silicate of (2), said compound of 2 is dispersed with components (1), (3) and/or (4) during preparation of said personal wash composition, and wherein said compound of 2 interacts with surfactant and lowers the viscosity of said composition.

2. A composition according to claim 1, comprising 0.5 to 10% cationic, non-silicate compound.

* * * * *